(12) United States Patent
Yang et al.

(10) Patent No.: US 8,298,390 B2
(45) Date of Patent: Oct. 30, 2012

(54) ELECTROCHEMICAL PROBES FOR CORROSION MONITORING IN HYDROGEN SULFIDE SYSTEMS AND METHODS OF AVOIDING THE EFFECT OF ELECTRON-CONDUCTING DEPOSITS

(76) Inventors: Xiaodong Sun Yang, San Antonio, TX (US); Lietai Yang, San Antonio, TX (US)

(*) Notice: Subject to any disclaimer, the term of this patent is extended or adjusted under 35 U.S.C. 154(b) by 639 days.

(21) Appl. No.: 12/313,950

(22) Filed: Nov. 26, 2008

(65) Prior Publication Data

US 2010/0126859 A1      May 27, 2010

(51) Int. Cl.
*G01N 27/26* (2006.01)
(52) U.S. Cl. .................. 204/404; 205/775.5
(58) Field of Classification Search .......... 204/404, 204/402; 205/122, 775.5; 324/700, 446
See application file for complete search history.

(56) References Cited

U.S. PATENT DOCUMENTS

| | | | |
|---|---|---|---|
| 4,412,174 A * | 10/1983 | Conlon et al. | 324/700 |
| 6,132,593 A | 10/2000 | Tan | |
| 6,683,463 B2 | 1/2004 | Yang et al. | |
| 7,180,309 B1 | 2/2007 | Yang | |
| 7,309,414 B2 | 12/2007 | Yang | |
| 2006/0189971 A1 * | 8/2006 | Tasto et al. | 606/32 |

OTHER PUBLICATIONS

Website : Corr Instruments "Localized Corrosion Analyzer and Multielectrode Probes" Available: http:www.web.archive.org/web/20040606101512/http://corrinstruments.com/inc.corprobes.html , Published Jun. 6, 2004.*
L. Yang, N. Sridhar, "Coupled Multielectrode Array Systems and Sensors for Real-Time Corrosion Monitoring—A Review," Corrosion NACExpo 2006 61st Annual Conference and Exposition, Paper #06681, Published Mar. 2006.*
S. Papavinasam, "Electrochemical Techniques for Corrosion Monitoring," in "Corrosion Monitoring Techniques," L. Yang, ed., Woodhead Publishing, Success, UK (2008), Section 3.8.3 and pp. 77 to 79].
L. Yang, "Multielectrode Systems," in "Corrosion Monitoring Techniques," L. Yang, ed., Woodhead Publishing, Success, UK, (2008), Section 8.8.2].
N. Sridhar, L. Yang and F. Song, "Application of Multielectrode Array to Study Dewpoint Corrosion in High Pressure Natural Gas Pipeline Environments", CORROSION/2006, paper No. 06673 (Houston, TX: NACE, 2006).

* cited by examiner

*Primary Examiner* — Jeffrey T Barton
*Assistant Examiner* — Louis Rufo (57) ABSTRACT

Electrochemical probes for corrosion monitoring in an environment that may cause the formation of electron-conducting deposits and the method for making such probes were described. The probes have long exposed electrodes. Except for the tip section, all surfaces of the exposed electrodes are coated with a coating or covered with electrically insulating tubing, so that only the tip section has uncovered metal that serves as the active areas of the electrodes. The coating or tubing material is such that the deposits cannot easily form on its surfaces. Because the electrical bridging between the active areas of any two electrodes requires the deposition of an evenly distributed layer of the electron-conducting deposits along the path from one area to the other area, the coated surface reduces the possibility of short-circuiting for the active areas of the electrodes. These probes are especially suitable for applications in systems containing hydrogen sulphide ($H_2S$).

17 Claims, 10 Drawing Sheets

A–A View
FIG. 5

Container Outside | Container Inside

ELECTROCHEMICAL PROBES FOR CORROSION MONITORING IN HYDROGEN SULFIDE SYSTEMS AND METHODS OF AVOIDING THE EFFECT OF ELECTRON-CONDUCTING DEPOSITS

TECHNICAL FIELD OF THE INVENTION

This invention relates to electrochemical probes for corrosion monitoring in systems such as those containing hydrogen sulfide that cause the formation of electron-conducting deposits on the sensing electrodes and leads to the short-circuiting between or among the electrodes.

BACKGROUND OF THE INVENTION

Coupled multielectrode array sensors (CMAS) (see U.S. Pat. No. 6,683,463, No. 6,132,593, and No. 7180309) and other electrochemical sensors for corrosion monitoring are subject to the bridging effect of the formation of electron-conducting deposits that causes the short-circuiting among the sensing electrodes [see S. Papavinasam, "Electrochemical Techniques for Corrosion Monitoring," in "Corrosion Monitoring Techniques," L. Yang, ed., Woodhead Publishing, Success, UK (2008), Section 3.8.3 and pages 77 to 79]. These electron-conducting deposits may be formed by the corrosion of iron in an environment containing hydrogen sulfide ($H_2S$), because the corrosion product (such as FeS) is a semiconductor material. When the sensing electrodes are short circuited, the corrosion current cannot be accurately derived by the current that is measured by the sensor instrument [see Lietai Yang, "Multielectrode Systems," in "Corrosion Monitoring Techniques," L. Yang, ed., Woodhead Publishing, Success, UK, (2008), Section 8.8.2]. Thus the sensor instrument cannot effectively measure the corrosion rate. A method to minimize the bridging effect is to increase the distance between the electrodes. Because of the size of the probes and the space of the measurement environment where the probe is installed, there is always a limit for the distance between the electrodes. This is especially true for the CMAS probes, because of the many electrodes it has. Another approach to minimize the bridging effect, in the case of a CMAS probe, is to reduce the resistance of the measuring circuit in the sensor instruments. However, there are challenges in the reduction of the resistance in the sensor instrument when the bridging effect is severe. This invention is related to the separation of the active sensing surface areas of the electrodes to avoid the formation of a continuous layer of electron-conducting deposits along the path between any pairs of the electrodes.

REFERENCE NUMBERS OF DRAWINGS

5   insulation material (usually epoxy or ceramic)
6   probe cable
8   electrical leads connected to electrodes (see 30 below)
10  probe
13  probe head
15  probe body
20  container wall (corrosive medium, including electron-conducting materials, is inside the container)
29  coating (or tubing) that is resistant to the formation of corrosion products on its surface
30  electrodes coated with the coating or covered by the tubing (or called coated electrodes)
31  uncoated electrode
35  active areas of electrodes
40  spacer
42  spacer body
43  spacer hole (to allow insertion of coated electrodes)
50  spacer squeezer
52  spacer squeezer support -continued

| | |
|---|---|
| 53 | spacer squeezer threads and screw for squeezing the spacer |
| 60 | spacer assembly |
| 62 | spacer assembly body |
| 63 | optional O-rings for sealing between the spacer assembly and probe |
| 64 | optional thread and screw for fixing spacer assembly to probe |
| 65 | thread and screw for fixing spacer to spacer assembly |
| 70 | solid deposits that may be electronic conducting |
| 80 | compression fitting at top of spacer assembly |
| 82 | top with thread for compression fitting |
| 84 | follower |
| 86 | sealant |
| 88 | compression fitting body |
| 90 | sealing weld between probe spacer assembly body and container wall |
| 92 | sealing thread between probe spacer assembly body and container wall |

DETAILED DESCRIPTIONS OF THE INVENTION

Figure 1:
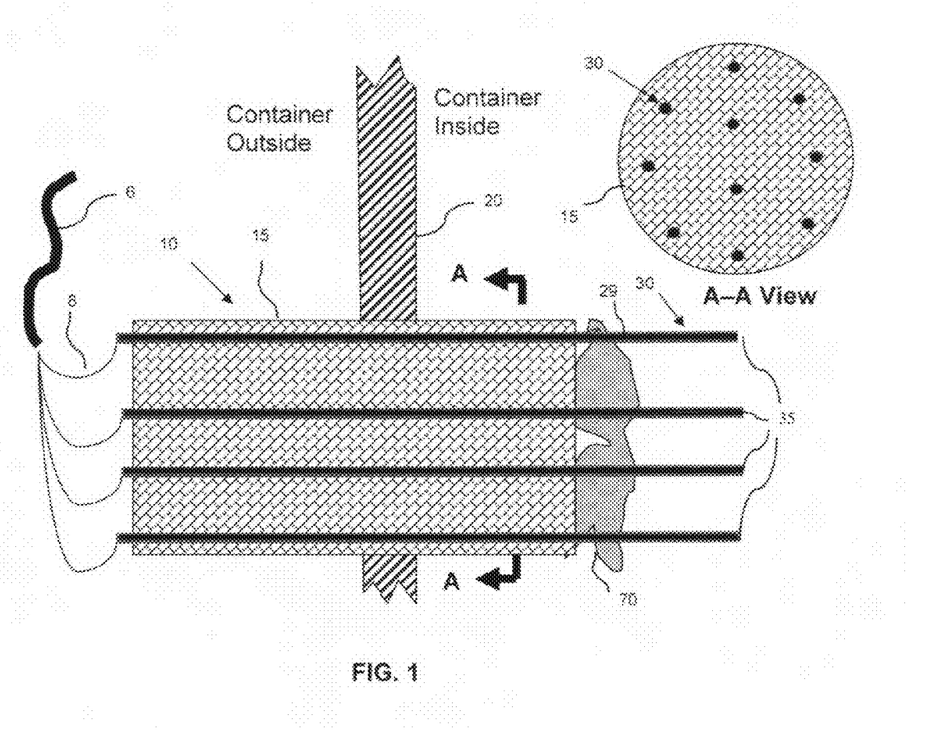
FIG. 1 illustrates a typical coupled multielectrode array sensor (CMAS) probe with coated electrodes to avoid the short circuiting among the electrodes by electron-conducting deposits.
Figure 2:
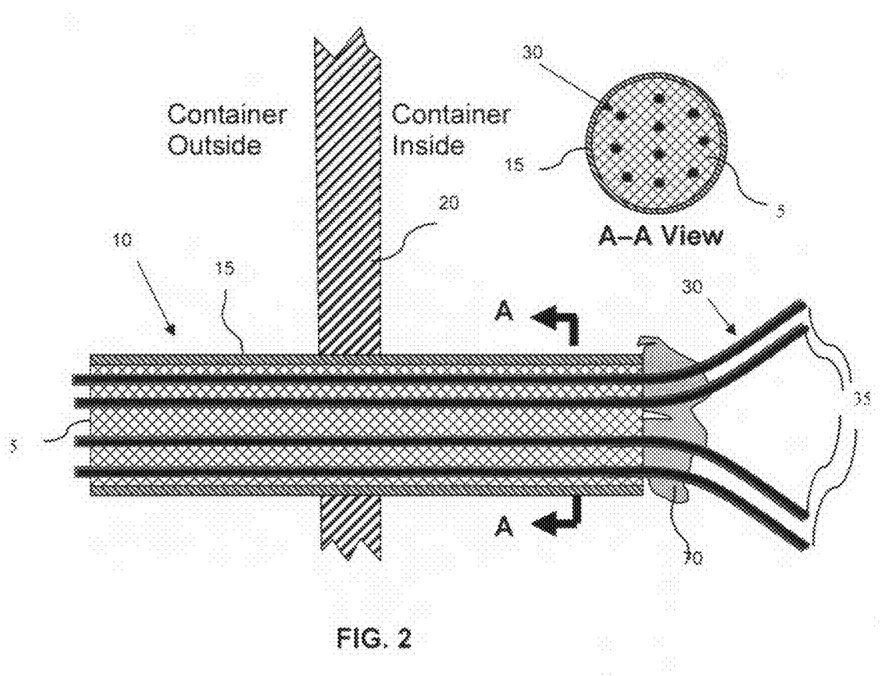
FIG. 2 illustrates a typical CMAS probe with coated electrodes that are curved away to further increase the distance among the electrodes to avoid the short circuiting among the electrodes by electron-conducting deposits.

CMAS Probes with Coated Electrodes
FIGS. 1 and 2

FIG. 1 shows a typical coupled multielectrode array sensor (CMAS) probe (10) that has coated electrodes to avoid the formation of electron-conducting deposits along the path from the active area of one electrode to the active areas of the other electrodes. In this design, the electrodes (30) are coated with (or covered by) a coating (or a plastic tubing) (29) and embedded in the probe body (15). The coated electrodes (30) are connected to the electrical cable (6) by the electrical leads (8). The coating (29) on the side surface of the coated electrode can be made of an epoxy, polytetrafluoroethylene (PTFE) tube, polyetheretherketone (PEEK) tube, or other polymer tube or paint that is resistant to the formation of corrosion product deposits (70) that may be electronic conducting. The electron-conducting solid deposits often form at the active areas (35) of the electrodes, if the probe is mounted to a container (20) that contains hydrogen sulfide. Unlike the surface of a corroded metal, which allows the easy attachment and build-up of corrosion product deposits (70), the coating surface is resistant to the attachment of the electron-conducting deposits so that the deposits cannot easily grow on the coating surfaces and form a continuous path that allows the electron to travel from the active area (35) of one electrode to the active areas (35) of one or more other electrodes. In addition, the smooth and noncorrodable coating surface allows the easy removal of the solid deposits (70) in the event they do form on the coating surface.

Figure 3A:
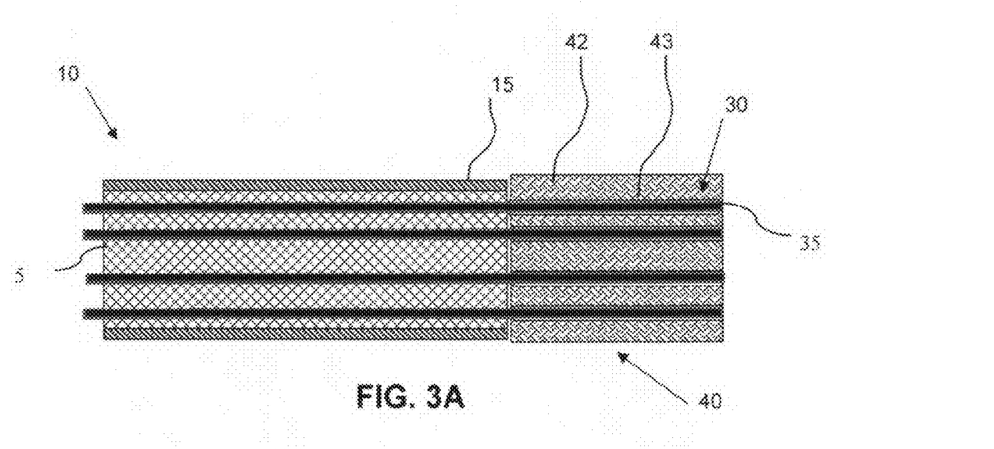
FIGS. 3A and 3B illustrate a typical CMAS probe with coated electrodes to avoid the short circuiting among the electrodes by electron-conducting deposits and a removable spacer to support the electrodes during polishing.
Figure 3B:
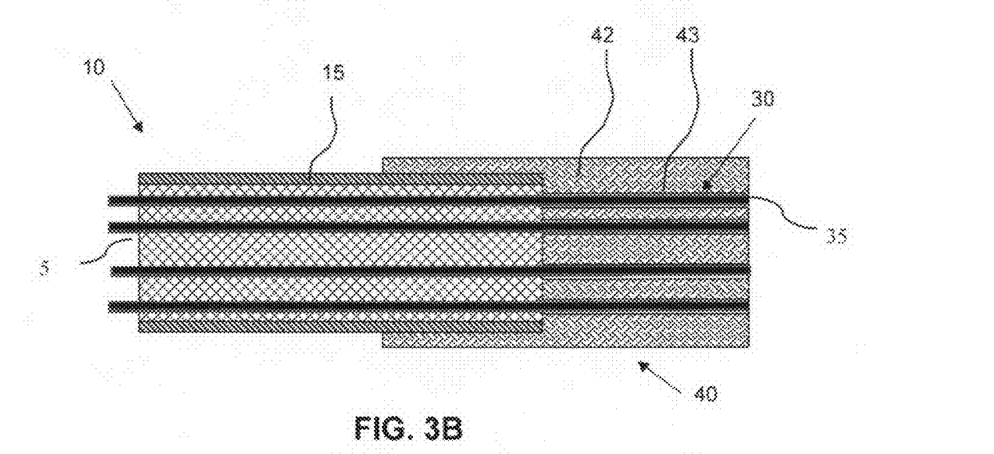

FIG. 2 illustrates a typical CMAS probe with coated electrodes that are curved away to increase the distance from the active area (35) of one electrode to the active area (35) of other electrodes to avoid the short circuiting of the active areas of the coated electrodes by electron-conducting deposits
FIGS. 3A, 3B, 4A, and 4B FIGS. 3A and 3B illustrate typical CMAS probes with coated electrodes to avoid the short circuiting of the active areas of the coated electrodes and a removable spacer (40) to support the electrodes during polishing. The spacer has a spacer body (42) and holes (43) that allow the electrode to go through and support the coated electrodes (30) during the polishing of the active areas (35) of the coated electrodes. Because the coated electrodes in a CMAS probe are usually thin and flexible, the spacer provides the convenient support for the flexible electrodes during polishing. Therefore, the spacer allows the probes to be easily polished and re-used many times. In FIG. 3B, the spacer body (42) has an extended recess hole of the same diameter as that of the probe body (15), at the left-hand side, so that the probe body (15) can be fitted into the recess when the spacer (40) is installed. The tight fit between the spacer body (42) and the probe body (15) makes it easier to polish the active areas (35) of the coated electrodes (30).

Figure 4A:
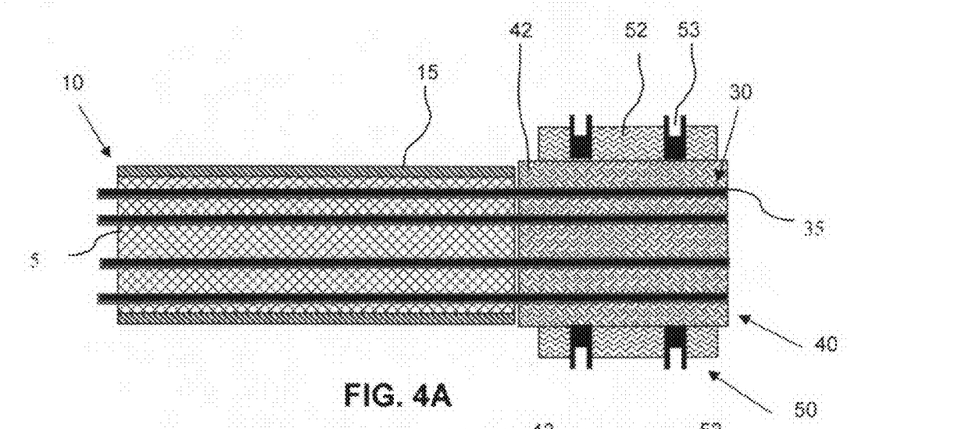
FIGS. 4A and 4B illustrate a typical CMAS probe with coated electrodes to avoid the short circuiting among the electrodes by electron-conducting deposits and a squeezable spacer to support the electrodes during polishing.
Figure 4B:
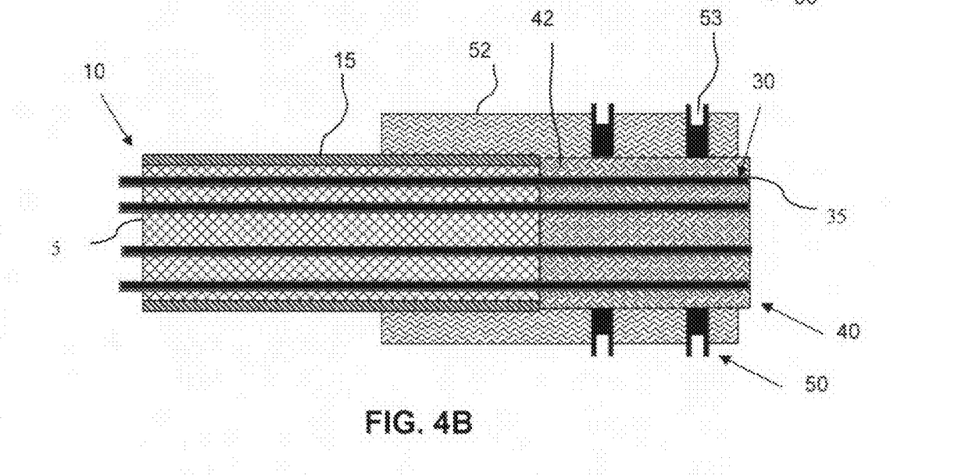

FIGS. 4A and 4B illustrate a typical CMAS probe with coated electrodes, to avoid the short circuiting of the active areas of the coated electrodes, and a squeezable spacer to support the electrodes during polishing. The squeezable spacer has a regular spacer (40) and a spacer squeezer (50). The spacer squeezer has a spacer squeezer support (52) and one or multiple threads and screws (53). When the screws (53) are tighten into the threaded holes, the spacer is squeezed onto the coated electrodes and tightly holds all coated electrodes for easier polishing of the active areas of the electrodes. Polishing allows the probe to be reused many times. In FIG. 4B, the spacer squeezer support (52) has an extended recess hole of the same diameter as that of the probe body (15), at the left-hand side, so that the probe body (15) can be fitted into the recess when the spacer (40) is installed. The tight fit between the spacer squeezer support (52) and the probe body (15) makes it easier to polish the active areas (35) of the coated electrodes (30).

Figure 5:
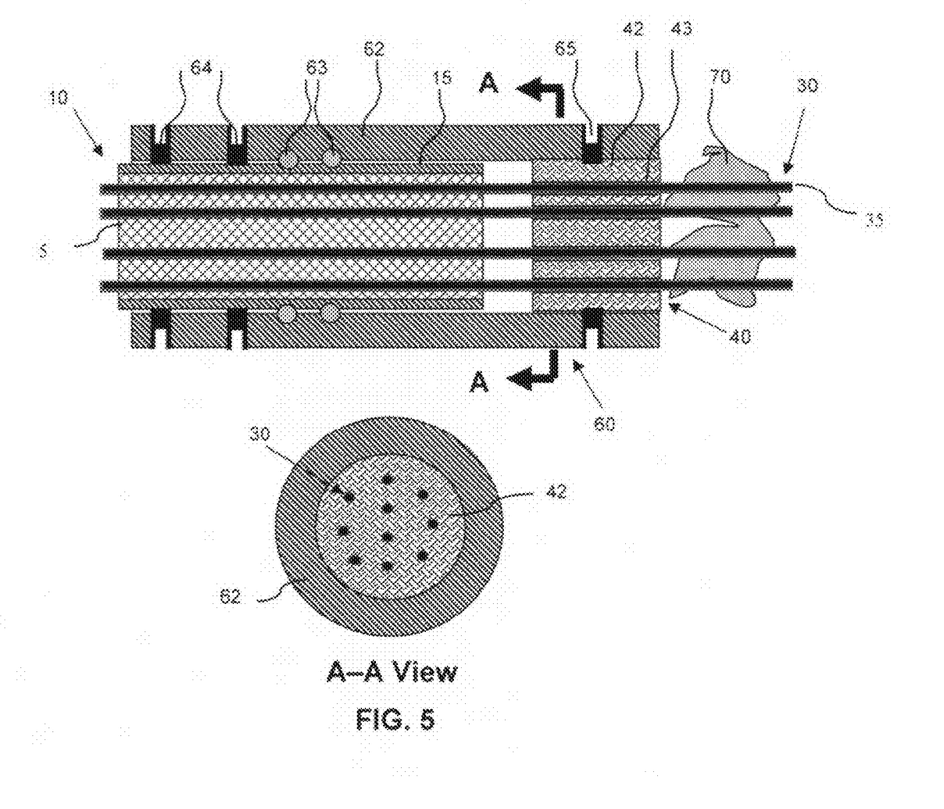
FIG. 5 illustrates a typical CMAS probe with coated electrodes to avoid the short circuiting among the electrodes by electron-conducting deposits and a depth adjustable spacer assembly that supports the electrodes during polishing and removes the electron-conducting deposits during service.
Figure 6:
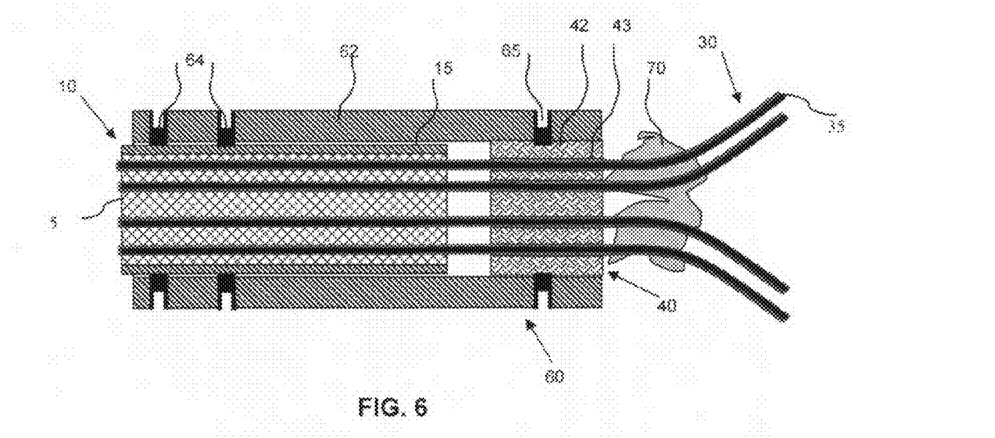
FIG. 6 illustrates a typical CMAS probe with coated electrodes that are curved away to increase the distance among the electrodes to avoid the short circuiting among the electrodes by electron-conducting deposits and a depth adjustable spacer assembly that supports the electrodes during polishing and removes the electron-conducting deposits during service.
Figure 7:
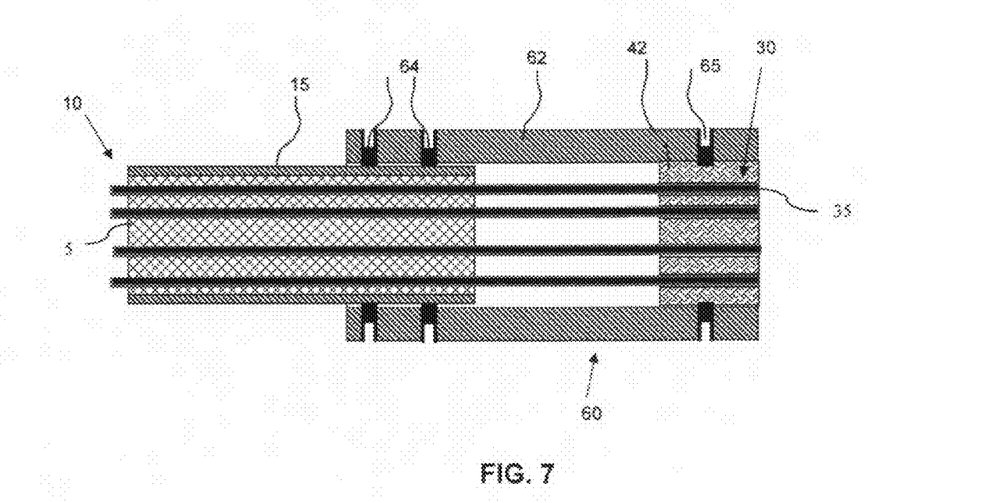
FIG. 7 illustrates the position of the spacer of a typical CMAS probe with coated electrodes and a depth adjustable spacer assembly during polishing of the electrodes.

CMAS Probes with Coated Electrodes and Depth-Adjustable Spacers
FIGS. 5, 6, and 7

FIGS. 5 and 6 illustrate typical CMAS probes with coated electrodes to avoid the short circuiting of the electrodes by electron-conducting deposits and a depth-adjustable spacer assembly (60). The spacer assembly (60) has a regular spacer (40) and a spacer assembly body (62). A set of optional O-rings (63) may be used to provide the sealing between the spacer assembly body (62) and the probe body (15). One or more optional sets of threads and screws (64) may be used to fix the spacer assembly (60) to the probe (10). A separate one or more threads and screws (65) are used to fix the spacer (40) to the spacer assembly body (62). During normal service of the probe, the spacer assembly is in the left position (as shown in FIGS. 5 and 6) so that the coated electrodes are fully exposed. During polishing, the spacer assembly (60) is adjusted to the right so that the end surface of the spacer (40) is aligned with the active areas (35) of electrodes thus allowing the spacer to provide support to the electrodes during the polishing process (see FIG. 7). If deposits are formed on the side surfaces of the coated electrodes, the deposits can be easily removed by moving the spacer assembly from the left to the right. The curved electrodes (as shown in FIG. 6) are flexible, so that the spacer assembly can be moved to the right (as shown in FIG. 7). The coated electrodes (30) usually have the memory feature, so that they will return to their curved positions after the spacer assembly is moved to the left position. The spacer body material should be softer than the coating (29) so that its edge does not damage the coating.
FIGS. 8, 9, and 10

Figure 8:
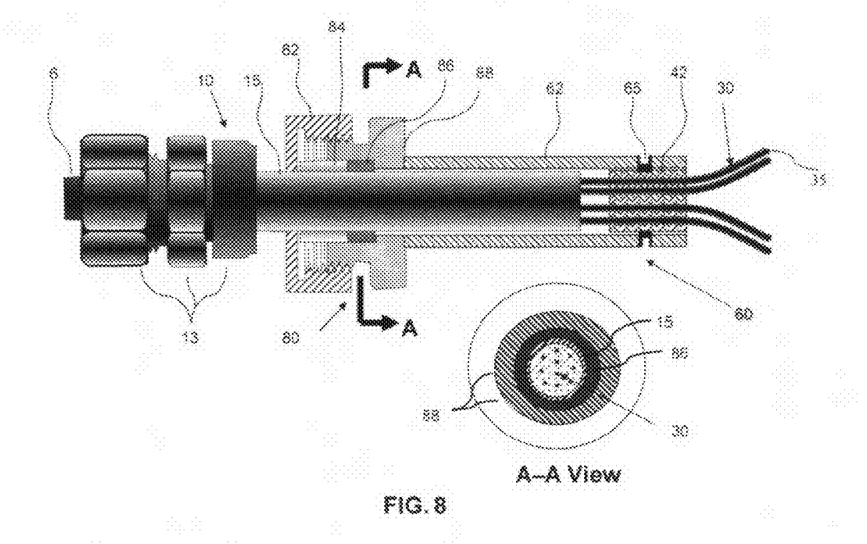
FIG. 8 illustrates a typical CMAS probe with coated electrodes to avoid the short circuiting among the electrodes by electron-conducting deposits and a depth adjustable spacer assembly that can be sealed onto the probe body at variable depth locations using a compression fitting.
Figure 9:
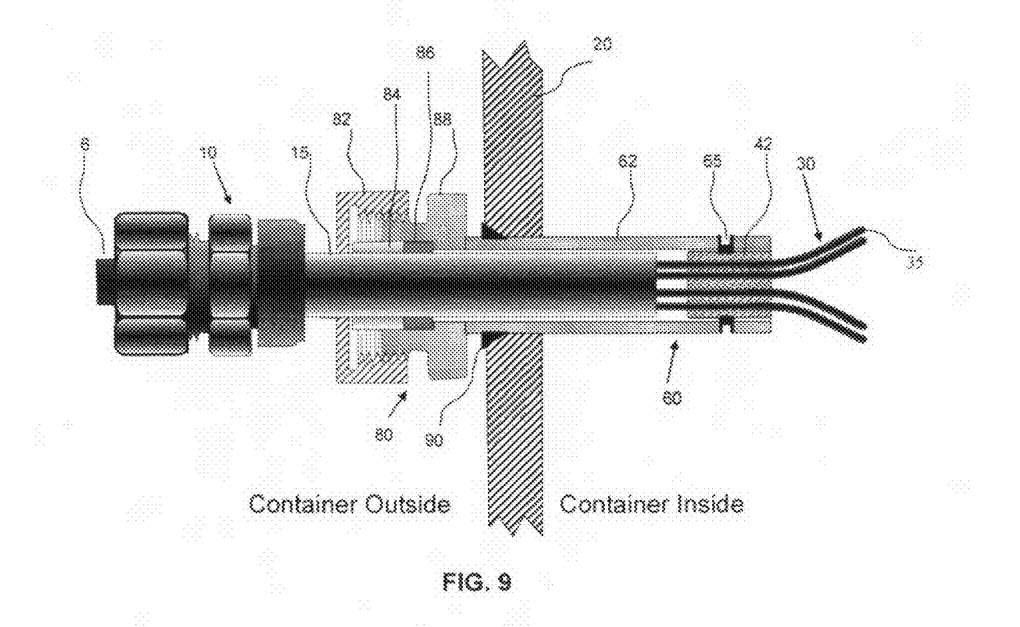
FIG. 9 illustrates the mounting of a typical CMAS probe with coated electrodes and a depth adjustable spacer assembly that can be sealed onto the probe body at variable locations using a compression fitting onto a reactor vessel with a weld joint.
Figure 10:
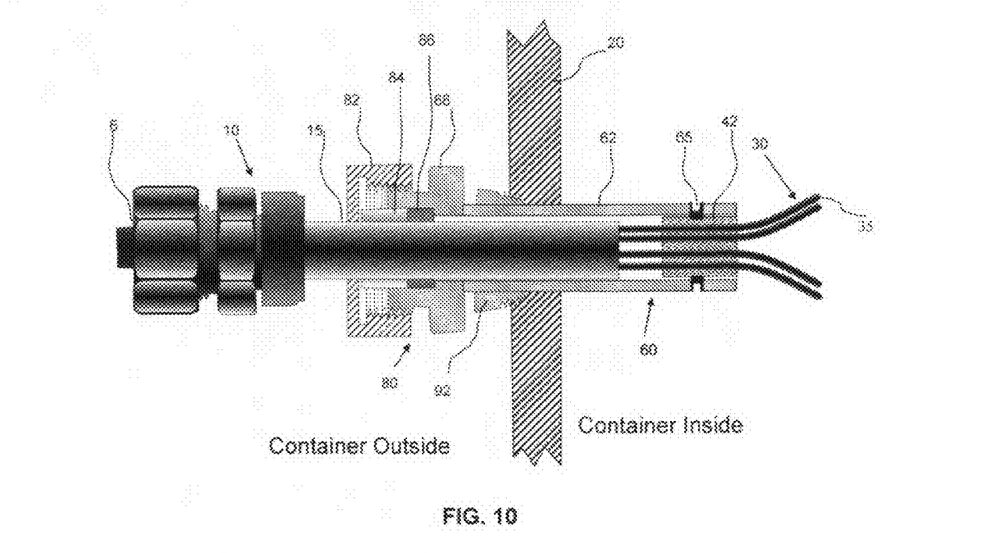
FIG. 10 illustrates the mounting of a typical CMAS probe with coated electrodes and a depth adjustable spacer assembly that can be sealed onto the probe body at variable locations using a compression fitting onto a reactor vessel with a threaded fitting.
Figure 11:
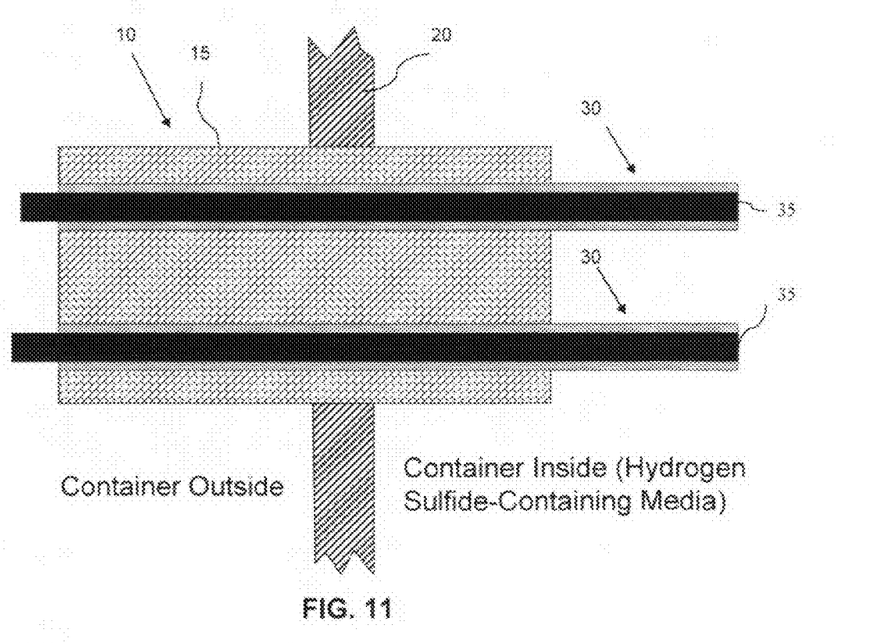
FIG. 11 illustrates a typical two-electrode electrochemical probe with coated electrodes to avoid the short circuiting between the electrodes by electron-conducting deposits.
Figure 12:
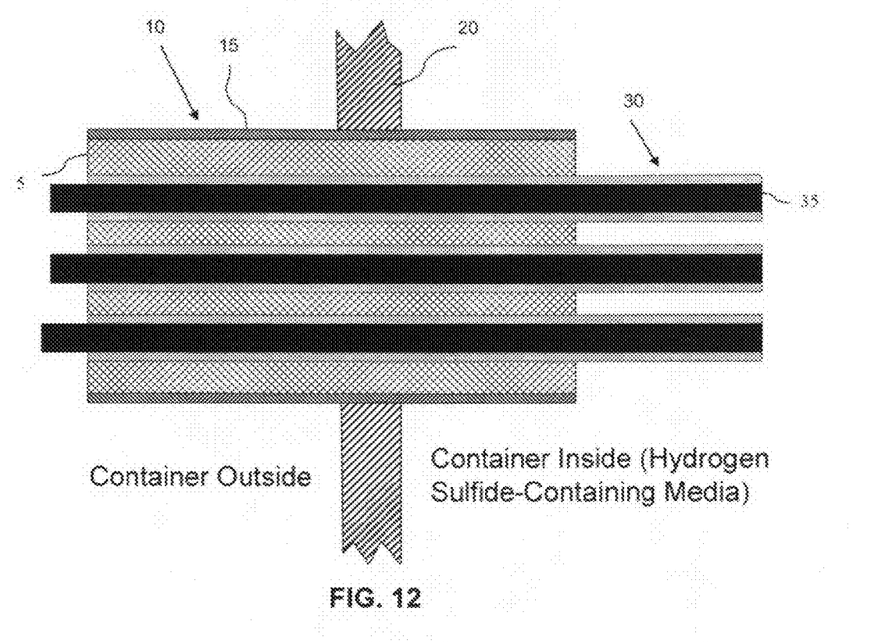
FIG. 12 illustrates a typical three-electrode electrochemical probe with coated electrodes to avoid the short circuiting among the electrodes by electron-conducting deposits.

FIG. 8 illustrates a typical CMAS probe (10) with coated electrodes, to avoid the short circuiting by electron-conducting deposits, and a depth-adjustable spacer assembly (60) that can be sealed onto the probe body at variable depth locations using a compression fitting (80). The compression fitting (80) is hermetically attached to the top of the spacer assembly (60). The compression fitting (80) has a top (82) that can be threaded to the compression fitting body (88). There is a rigid follower (84) between the top (82) and the sealant (86). When the top (82) is torqued to the compression fitting body (88), the follower (84) presses the sealant (86) onto the probe body (15) to form a hermetic seal between the probe (10) and the spacer assembly (60). The system (as shown in FIG. 8) can be mounted to a high pressure container by a sealing weld joint (90) (see FIG. 9) or threaded joint (92) (see FIG. 10) between the spacer assembly body (62) and the container wall (20). The probe (10) can be conveniently moved up or down the spacer assembly (60) that is fixed onto the container wall, to remove the corrosion products (70) that may be formed during the service of the probe. During the normal service, the probe (10) is in a position (as shown in FIGS. 9 and 10) to avoid the bridging between the active area (35) of one electrode and the active areas (35) of the other electrodes. When the corrosion products are formed—or are suspected to have formed—at the probe tip, these corrosion products can be cleaned by moving the probe (10) up and down so that the corrosion products are removed by the spacer (40).

The active area (35) of the coated electrodes can be polished with the spacer assembly (60) being positioned such that the surface of the spacer (40) is aligned with the active area surface (35) of the coated electrodes (30). In this location, the spacer provides rigid support during the polishing of the active area of the coated electrodes.

Other Electrochemical Probes with Coated Electrodes
FIGS. 11, 12, 13, and 14

Figure 13:
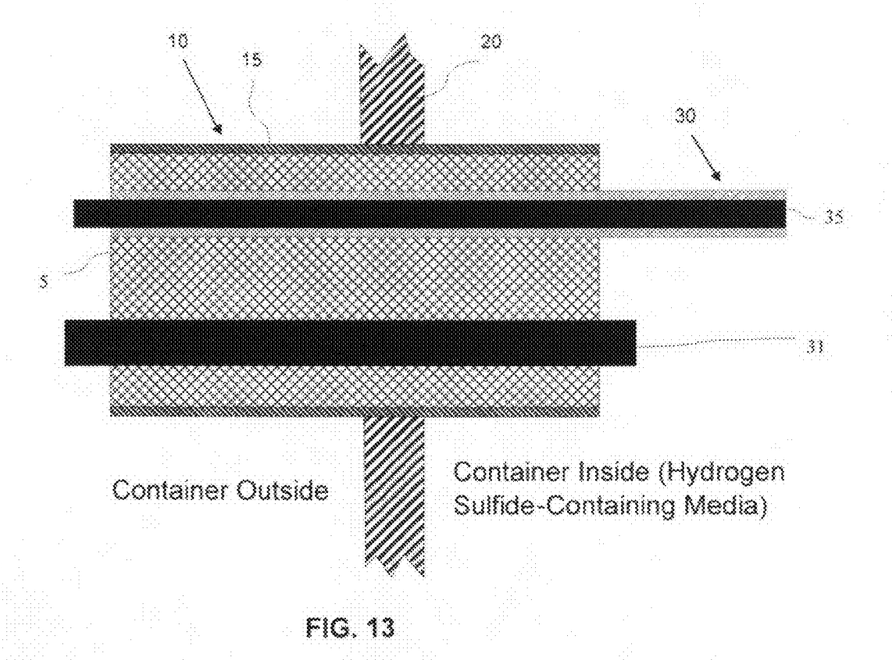
FIG. 13 illustrates a typical electrochemical probe with only one coated electrode to avoid the short circuiting among the electrodes by electron-conducting deposits.

The concept of using coated electrodes, so that it is resistant to the formation of electron-conducting deposits to minimize the bridging effect in hydrogen sulfide environments, may also be applied to other electrochemical sensors, such as two-electrode (FIG. 11) and three-electrode (FIG. 12) probes. These two- or three-electrode configurations are often found in linear polarization resistance (LPR) probes, galvanic probes, electrochemical noise probes, electrochemical impedance spectroscopy probes, and zero-ammetry probes. Some probes may even have only one coated electrodes (as shown in FIG. 13) where the auxiliary electrode (31) is not coated.

Figure 14:
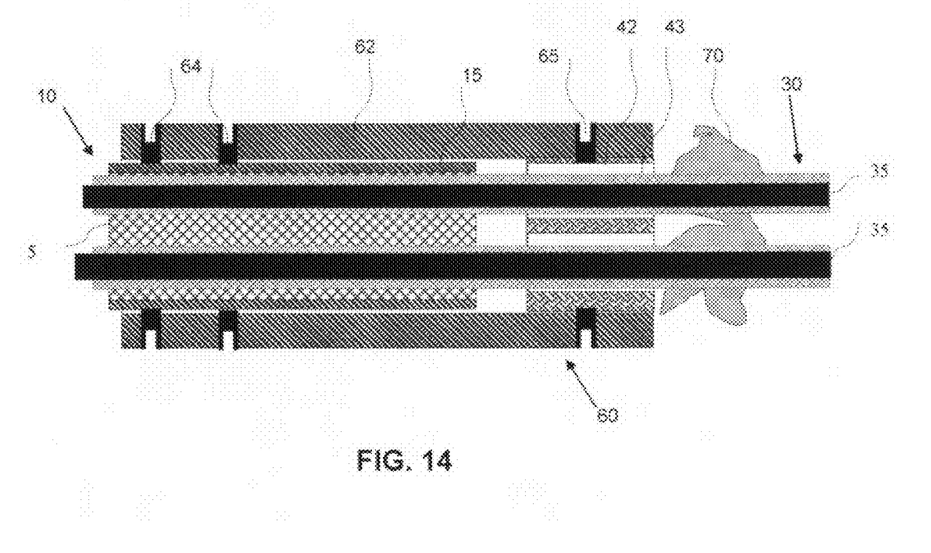
FIG. 14 illustrates a typical two-electrode electrochemical probe with coated electrodes to avoid the short circuiting among the electrodes by electron-conducting deposits and a spacer assembly that supports the electrodes during polishing and removes the electron-conducting deposits.

FIG. 14 illustrates a typical two-electrode electrochemical probe with coated electrodes, to avoid short circuiting, and a spacer assembly that supports the electrodes during polishing. The spacer assembly can also be used to remove electron-conducting deposits, if they form on the coated electrodes.

Example Test Results

Two CMAS probes were used in the tests. One is an 8-electrode carbon steel probe, as shown in FIG. 1 [without the container wall (20)]. The other one is an 8-electrode regular carbon steel probe with flush-mounted electrodes. The active areas (35) of the regular probe were aligned with right-hand side surfaces of the probe body (15). The diameter of the carbon steel electrodes was 1 mm. The probe insulation (5) was epoxy. The outside diameter of the probe body was ¾" (19 mm). The exposed length of the coated electrodes (30) was 1" (25.4 mm). Thin PTFE tubes (about 1.2 mm OD, from Small Parts, Inc., Miramar, Fla., USA) were used as the coating for the probe with coated electrodes.

325-mesh copper powder was mixed with a small amount of wet clay (approximately 10% by weight on dry basis) obtained from a local garden. The copper powder was washed with a 10% (by weight) hydrochloric acid solution, to remove the oxide film before the mixing. The tips of the two probes were dipped into the wet copper-clay mixture for a short duration and then removed. Solid deposits (as shown in FIG. 1) were formed on the two probes. No deposits were visually observed on the exposed section of the coated electrodes near the active areas. A multimeter (Model 2700 from Keithley Instruments, Inc., Cleveland, Ohio, USA) was used to measure the resistance between each electrode and the joint where all other electrodes were connected. The connection joint is equivalent to the coupling joint in a CMAS probe. Table 1 shows the measured results.

TABLE 1

Resistance between individual electrodes and the other electrodes that were coupled to a common joint after the probes were dipped into a wet and sticky electron-conducting mixture (ohm).

| Electrode | 1 | 2 | 3 | 4 | 5 | 6 | 7 | 8 |
|---|---|---|---|---|---|---|---|---|
| Coated Probe | O.L.* | O.L. | O.L. | O.L. | O.L. | O.L. | O.L. | O.L. |
| Regular Probe | 0.3 | 0.4 | 0.3 | 0.3 | 0.4 | 0.5 | 0.3 | 0.4 |

*O.L. stands for out of limits (>10 GOhm).

As shown in Table 1, the PTFE coating on the coated electrodes effectively prevented the formation of a continuously distributed layer of electron-conducting deposits along the path from the active area (35) of any of the electrodes to the active areas of the other electrodes. In contrast, the electron-conducting deposits easily formed on the active areas of the regular probe, and the deposits covered all the active area of the electrodes and caused short-circuiting for the electrodes.

OTHER EMBODIMENTS

The coated probes are mainly described for use in hydrogen sulfide environments that cause the formation of corrosion products that would short circuit the electrode. The probes with coated electrodes may also be used in other environments that may cause the formation of electron-conducting deposits. These environments include the engine exhaust system where carbon deposits may be formed to cause the short-circuiting.

Although the present invention has been described in detail, it should be understood that various changes, substitutions, and alterations can be made hereto, without departing from the spirit and scope of the invention as defined by the appended claims.

The invention claimed is:
1. An electrochemical probe for corrosion monitoring in an environment that may cause the formation of electron-conducting deposits on the probe, comprising:
    (a) a plurality of electrodes;
    (b) a body wherein a portion of each electrode is embedded to form a probe and the remaining portion of the electrodes is exposed out of the probe body;
    (c) electrical leads connected individually to each electrode at the end of the electrodes that are being embedded; and
    (d) a coating that is chemically and mechanically stable in said environment;
    wherein the coating is applied to the electrodes, such that all surface areas of each exposed electrode—except for a polished area at the electrode tip that serves as the active area of the electrode—is covered by the coating and the electrodes are spaced such that there are gaps between the outside surfaces of the coatings of the adjacent electrodes near the active areas to prevent the formation of evenly distributed electron-conducting deposits on the electrodes to cause short-circuiting between any two active areas.
2. The electrochemical probe of claim 1, wherein said probe is a multielectrode probe that contains 4 or more electrodes.

3. The electrochemical probe of claim 1, wherein said coating is a thin electrically insulating tubing.

4. The electrochemical probe of claim 1, wherein said coating is epoxy.

5. The electrochemical probe of claim 1, wherein some active areas are larger than the other active areas.

6. The electrochemical probe of claim 1, wherein one or more active areas are larger than another active area.

7. The electrochemical probe of claim 1, wherein the exposed section of the electrodes is bent so that the distance from the active area of one electrode to the active area of any of the other electrodes is larger than when the electrodes are straight to prevent short circuiting by a large piece of deposit that may be formed at the tip section of the probe.

8. The electrochemical probe of claim 1, wherein a removable spacer with holes that allow the exposed electrodes to easily go through is added.

9. The electrochemical probe of claim 8, wherein the spacer is attached to a spacer assembly that can be moved up or down along the probe and can be fixed to the probe body at variable depth locations.

10. The electrochemical probe of claim 8, wherein the spacer is attached to a spacer assembly that can be moved up or down along the probe and sealed onto the probe body at variable depth locations.

11. The electrochemical probe of claim 10, wherein the spacer assembly is mounted to the wall of a vessel.

12. A method to form an electrochemical probe that avoids the bridging effect by electron-conducting deposits that may be formed on the probe electrodes in a corrosive medium, comprising the steps of:
   a) connecting the electrodes to metal electrical leads;
   b) embedding a portion of the electrodes at the end connected to the electrical leads in a probe body to form the probe and leave the other portion exposed; and
   c) coating the exposed section of a pre-selected number of electrodes, but leaving out a polished area at the tip which is used as the active area;
   wherein, the electrodes are spaced such that there are gaps between the outside surfaces of the coatings of the adjacent electrodes near the active areas to prevent the formation of evenly distributed electron-conducting deposits on the electrodes, which may cause short-circuiting between the active area of one electrode and the active area of another electrode.

13. The method of claim 12, wherein the probe has two or three electrodes.

14. The method of claim 12, wherein the pre-selected number is 1 or more.

15. The method of claim 12, wherein the coating is epoxy.

16. The method of claim 12, wherein the coating is tubing.

17. The method of claim 12, wherein the corrosive medium contains hydrogen sulphide.

* * * * *